(12) United States Patent
Mittal

(10) Patent No.: US 8,771,298 B2
(45) Date of Patent: Jul. 8, 2014

(54) TREATMENT OF SPHINCTER DYSFUNCTION

(75) Inventor: Ravinder K. Mittal, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 196 days.

(21) Appl. No.: 13/319,988

(22) PCT Filed: May 12, 2010

(86) PCT No.: PCT/US2010/034558
§ 371 (c)(1),
(2), (4) Date: Feb. 29, 2012

(87) PCT Pub. No.: WO2010/132574
PCT Pub. Date: Nov. 18, 2010

(65) Prior Publication Data
US 2012/0150195 A1    Jun. 14, 2012

Related U.S. Application Data

(60) Provisional application No. 61/177,913, filed on May 13, 2009.

(51) Int. Cl.
*A61B 17/08* (2006.01)
*A61B 17/00* (2006.01)
*A61B 17/04* (2006.01)
*A61B 17/072* (2006.01)
*A61F 2/00* (2006.01)

(52) U.S. Cl.
CPC ....... *A61B 17/00234* (2013.01); *A61B 17/0469* (2013.01); *A61B 17/072* (2013.01); *A61B 2017/00818* (2013.01); *A61F 2/0036* (2013.01)

USPC .......................................... 606/151; 606/139

(58) Field of Classification Search
USPC ......... 606/151, 153, 139, 142, 159, 180, 197; 604/271; 600/29, 30
See application file for complete search history.

(56) References Cited

U.S. PATENT DOCUMENTS

| | | | |
|---|---|---|---|
| 6,254,642 B1 * | 7/2001 | Taylor | 623/23.64 |
| 6,315,713 B1 | 11/2001 | Takada | |
| 6,544,271 B1 * | 4/2003 | Adams et al. | 606/139 |
| 7,083,629 B2 * | 8/2006 | Weller et al. | 606/151 |
| 7,306,614 B2 * | 12/2007 | Weller et al. | 606/151 |

(Continued)

FOREIGN PATENT DOCUMENTS

WO    2007-032776 A1    3/2007

OTHER PUBLICATIONS

PCT International Search Report for PCT Application PCT/US2010/034558, May 12, 2010.

*Primary Examiner* — Melanie Tyson
*Assistant Examiner* — Katelyn Bernier
(74) *Attorney, Agent, or Firm* — AlbertDhand LLP

(57) ABSTRACT

A dysfunctional sphincter muscle may be treated by shortening the muscle to plicate it and restore its functionality. Plicating the sphincter muscle as described effectively shortens the muscle and permits the muscle to perform its function of closing off the body passage or opening with which it is associated without conventional surgery to expose the sphincter muscle and shorten it. Thus, treatment for incontinence can be achieved by shortening the associated sphincter muscle without surgery that exposes the muscle itself and requires the surgeon to manually grab hold of the muscle and shorten it.

3 Claims, 7 Drawing Sheets

Spiral tool for anal sphincterplication

(56) References Cited

U.S. PATENT DOCUMENTS

| | | | |
|---|---|---|---|
| 2002/0082621 A1* | 6/2002 | Schurr et al. .................. 606/151 |
| 2003/0130559 A1 | 7/2003 | Morin et al. |
| 2003/0158563 A1* | 8/2003 | McClellan et al. ........... 606/151 |
| 2004/0193190 A1* | 9/2004 | Liddicoat et al. ............. 606/153 |
| 2007/0293857 A1 | 12/2007 | Blind et al. |
| 2008/0039874 A1* | 2/2008 | Catanese et al. .............. 606/142 |
| 2008/0249538 A1* | 10/2008 | Kraemer et al. .............. 606/140 |
| 2008/0275306 A1 | 11/2008 | Rebuffat et al. |

* cited by examiner

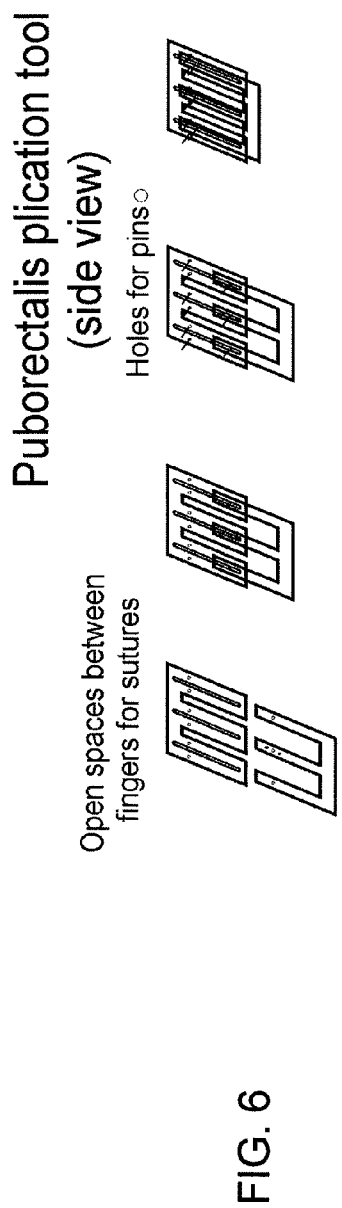
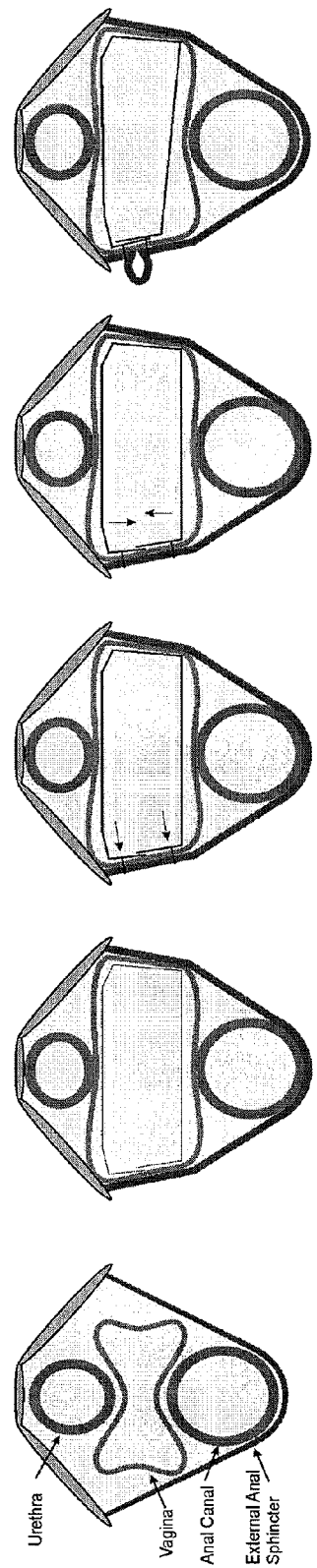
FIG. 6

TREATMENT OF SPHINCTER DYSFUNCTION

BACKGROUND

Sphincter muscles are generally circular, ring-shaped muscles that can contract to close off a body passage or opening. Sphincter muscles are located in many parts of the body, including locations associated with the esophagus, epiglottis, stomach, urethra, upper intestine, lower intestine, anus, and bladder, among others. A sphincter muscle typically surrounds a portion of tissue comprising a passage or opening of the body, such as a canal or tract, and controls passage of bodily fluids by contracting. Passage of bodily fluids into or out of the associated passages and openings cannot be sufficiently controlled if the sphincter muscle suffers from dysfunction or damage. For example, fecal incontinence can result from problems with the anal sphincter. The anal sphincter can become weakened or damaged from rectal prolapse or, in women, during childbirth. Urinary incontinence can result from problems with the sphincter muscles associated with the bladder or urethra. Dysfunction of other sphincter muscles can result in similar incontinent conditions or difficulties with bodily functions.

Medications, dietary changes, biodfeedback, and similar treatments may be insufficient to correct a dysfunctional sphincter muscle. In those situations, surgery might be necessary to repair the sphincter muscle and restore normal functioning. Surgery for repair of a sphincter muscle typically involves external sphincteroplasty, a shortening of the sphincter to ensure that it can properly close off its associated body passage or opening. The sphincter has an axial length, along the axis of the associated passage or opening, and has a circumferential length. Currently, surgery to repair a sphincter muscle begins with incisions to expose the muscle itself, followed by shortening the circumferential length of the sphincter muscle by the surgeon manually grabbing hold of the muscle and cutting or opening the sphincter muscle, removing a circumferential segment of the sphincter, and then re-joining the cut ends with a suture or staple.

The extent of muscle shortening from the surgery can be difficult to determine, because the muscle is in a non-functioning condition from being surgically exposed. Post-operative treatment requires careful control of infection risk at the wound site surrounding the sphincter muscle. Unfortunately, some such sphincteroplasty procedures are not especially effective. Some ineffectiveness can be the result of, for example, the difficulty of determining the extent of muscle shortening from the surgical procedure.

Making incisions and exposing the sphincter muscle is a relatively invasive procedure that requires care and attention to operating resources and surgical procedures, control of infection, and post-operative recovery treatment. A less invasive treatment for sphincter dysfunction could save costs, reduce the risks of surgery, provide efficacious results, and be better tolerated by patients. There is a need for treatment of dysfunctional sphincter muscles that meets these requirements.

SUMMARY

Embodiments described herein provide a technique for treatment of a dysfunctional sphincter muscle by shortening the muscle to plicate it and restore functionality. Plicating the sphincter muscle effectively shortens the muscle and permits the muscle to perform its function of closing off the body passage or opening with which it is associated. The plication technique does not require surgery to expose the sphincter muscle. Rather, a suitable tool can be inserted into the passage or opening associated with the sphincter muscle to engage the sphincter muscle internally and move two locations of the muscle closer together. Moving the two locations of the sphincter muscle closer together forms a loop or pleat in the muscle, shortening or stretching the muscle. The tool can be manipulated so that the extent of moving the two locations of sphincter muscle together can be accurately determined with the sphincter muscle in its functional position, instead of being surgically exposed. After the loop or pleat of sphincter muscle is formed, the loop or pleat can be held fixed in place so that the muscle once again can close off the passage or opening with which the muscle is associated, thereby restoring desired performance and control. The fixing of the loop or pleat can be performed through an interior space (lumen) of the tool, through which a suture or surgical staple can be applied to hold the loop or pleat in place. Thus, the sphincter muscle is plicated by adjusting the length of the sphincter muscle through an intra-cavity or intraluminal technique. In this way, a dysfunctional sphincter muscle can be treated with a procedure that is less invasive than current surgical techniques. The procedure can be performed on an outpatient basis, thus it has reduced cost as compared with current surgical treatment, and thereby reduces risks of surgery. The technique is better tolerated by patients than current surgical treatment. The plication technique described herein provides efficacious results and permits superior control over the degree of shortening or overlap of the muscle, because the shortening or overlap occurs with the muscle in place for functioning, rather than exposed for surgery. The plication technique can be used to treat, for example, fecal incontinence, urinary incontinence, and vaginal laxity by treating the anal canal, urethra, and vaginal canal, respectively.

One suitable embodiment of a plication tool to perform the technique described herein has a substantially cylindrical shape comprised of two concentric sleeves. The tool is inserted into the passage or opening controlled by the sphincter muscle to lie within the axial length of the muscle. Pins are extended radially outward from the sleeves in at least two circumferential locations axially separated along the axial length of the sphincter muscle to engage the muscle, such as by piercing, so that the pins will not move relative to the sphincter muscle. The pins are then moved closer together, thereby moving the sphincter muscle with them and stretching the sphincter muscle, forming a loop or pleat of sphincter muscle that extends outwardly between the two pins. The outwardly extending loop of sphincter muscle is then held fixed by fastening the loop such as with sutures or staples. The pins are then retracted and the tool is withdrawn from the passage or opening.

Another suitable form of tool can be configured as a substantially cylindrical tool that is coiled on itself such that the pins can be moved closer together once the tool is inserted in the body passage or opening. Again, the pins are extended to engage the sphincter muscle so the pins do not move relative to the muscle. The tool is then coiled on itself, thereby moving the pins closer together and moving the sphincter muscle with them, forming an outwardly extending loop or pleat of sphincter muscle that is then held fixed. When coiled on itself, loose ends of the tool may overlap each other. For sphincter muscles that are U-shaped or semicircular, a suitable tool can be configured with a suitable shape such as a squared-off shape or a semicircular shape that is open-ended so that pins can be extended outwardly from the tool to engage the sphincter muscle and then be moved closer together, thereby forming a loop or pleat of sphincter muscle that can be fixed in place. After the sphincter loop is fixed, the tool can be withdrawn.

Other features and advantages of the present invention should be apparent from the following description of the preferred embodiments, which illustrate, by way of example, the principles of the invention.

BRIEF DESCRIPTION OF THE DRAWINGS

FIG. 6 is a depiction of a plication tool and a cross-sectional depiction of the puborectalis muscle undergoing plication as described herein with the illustrated tool.

DETAILED DESCRIPTION

Figure 1:
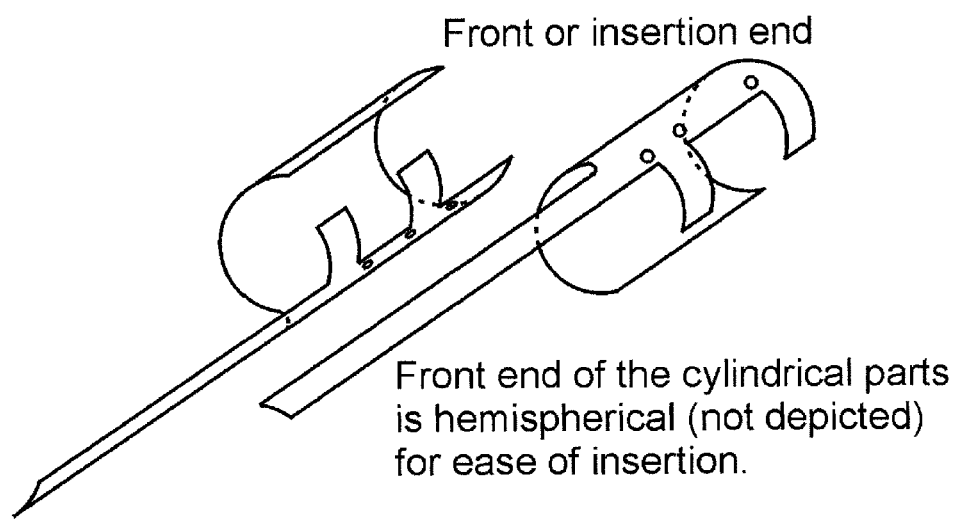
FIG. 1 shows a tool constructed to perform the sphincter treatment technique described herein.

In accordance with the techniques described herein, a dysfunctional sphincter muscle may be treated by shortening the muscle to plicate it and restore its functionality. Plicating the sphincter muscle as described herein effectively shortens the muscle and permits the muscle to perform its function of closing off the body passage or opening with which it is associated without conventional surgery to expose the sphincter muscle and shorten it. Thus, treatment for incontinence can be achieved by shortening the associated sphincter muscle without surgery that exposes the muscle itself and requires the surgeon to manually grab hold of the muscle and shorten it. The drawings show various embodiments of plication tools for use with the treatment technique. The examples illustrated in the drawings show plication tools for use in connection with two types of sphincter treatment: (1) anal sphincter and (2) puborectalis/pelvic floor muscle.

Introduction

Three versions of sphincter plication tools for the anal canal are described. The first version includes two concentric cylindrical sleeves that slide inside the anal canal, with either two sets of pins or four sets of pins. The second version of the tool is a unitary helical (i.e., circular cross-section) sleeve that has a similar construction as the first version with two sets of pins. The last version of plication tool described is suitable for the puborectalis muscle plication technique and is similar to the helical configuration but has a squared-off cross-sectional shape and is inserted into the vagina rather than the anal canal. In all of the illustrated tool versions, each set of pins are placed circumferentially about the same orientation but axially separated along the axial length of the muscle. These pins when extended into the sphincter muscle act as a means to engage or grab the muscle and then bring the ends of a section between the pins closer together. Instruments such as these described and those of similar configuration can be used to treat a variety of sphincter muscles. For example, such tools can adjust the length of the urinary sphincter, by placing the tool through the urethra, to treat urinary incontinence. Such tools can be used to adjust the length of the lower esophageal sphincter, by placing the tool through the mouth and esophagus to treat gastroesophageal reflux disease.

General Principle of Design

The basic idea behind these devices is to insert a tool that is hollow in the middle (to allow space for manipulation of staples and sutures) and that has retractable, radially oriented pins. During the insertion the pins are retracted in the central hollow space. After the insertion into the cavity the pin-hole position is oriented such that the segment of the muscle/sphincter that will be plicated is between the pin positions. The pins are then pushed all the way radially out to pierce through the wall of the passage or opening and into the sphincter muscle. The sleeve is then manipulated to bring the pins closer to each other in a plication position. The pins engage the sphincter muscle by piercing, so that the pins will not move relative to the sphincter muscle when the pins are brought closer together. Bringing the pins closer together results in stretching most of the muscle and creating a small part of the muscle that loops together between the pins. This maneuver in some tool designs will result in a smaller internal working space, in others it will not change. Once the pins are brought closer, there is some open space left between the pins where the tissue between the pins can be accessed for the purpose of suturing or stapling. Through the open spaces or windows sutures or staples are attached to plicate the muscle/sphincter. Finally, the pins are retracted back into the central hollow area and the tool removed.

First Implementation—Anal Canal

FIG. 1 shows a tool comprising two cylindrical sections with a handle and pin arrangement. The two cylindrical sections form a hollow space (lumen) within the device to provide an area from which sutures or staples may be applied to the sphincter muscle. With the handles in the open position the pins are retracted inside the lumen of the device (i.e., within the hollow space). This configuration places the tool in an insertion position that is suitable for inserting the tool into a bodily passage or opening for repair of the associated muscle. Once inserted into the passage or opening, the tool can be manipulated into a plication position in which the pins are extended to engage the sphincter muscle.

Figure 2:
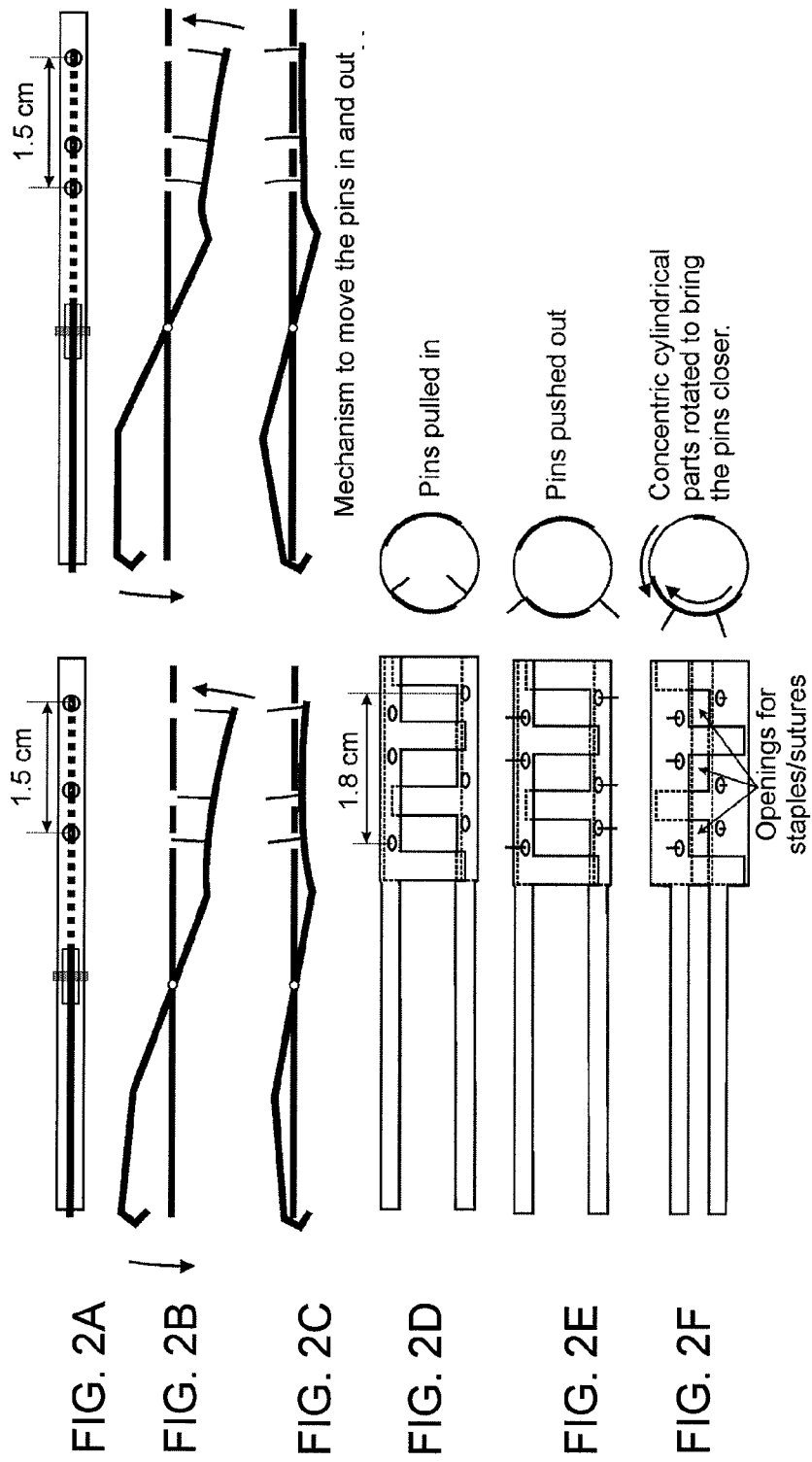
FIG. 2 shows the FIG. 1 tool in different stages of operation to perform the placation technique described herein.

Disassembled parts for the plication tool are shown in the figures. FIG. 2 shows one technique of inserting and retracting the pins. Dimensions are given as exemplary only; other dimensions will apply for work with different sphincter muscles, as will be known to those skilled in the art. With the handle in the insertion position the pins are retracted inside the lumen of the device (i.e., the hollow space within the device). The handle and pin arrangement are more clearly seen in FIG. 1, where the handles and pins are shown as part of the two cylindrical portions. FIG. 1 also shows that the two cylindrical portions have two claw-like parts that align with each other when assembled. The two cylindrical portions have similar curvatures, so that one can slide within the other and thereby the two guide movement relative to each other between the insertion position and the plication position.

Figure 3:
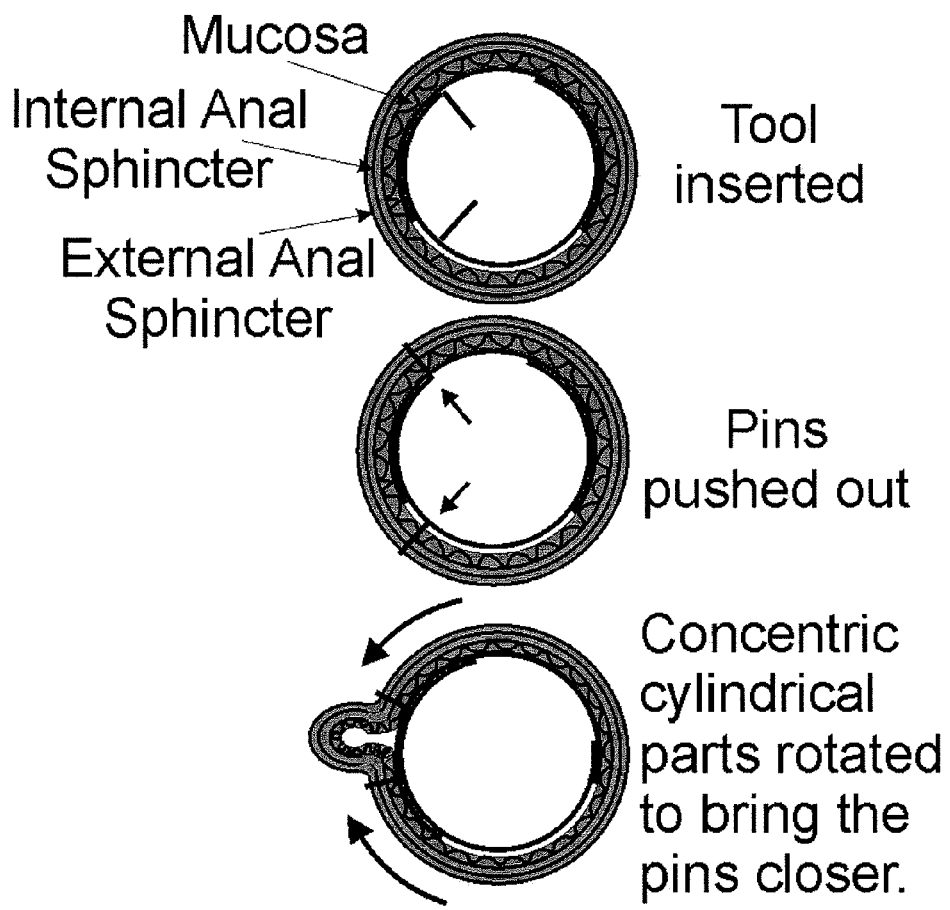
FIG. 3 is a cross-sectional depiction of a sphincter muscle that is plicated using the tool illustrated in FIG. 1 and FIG. 2.

The assembled condition of the two portions is more clearly seen in the lower part of FIG. 2 (FIGS. 2D, 2E, 2F). FIG. 2A-2F show the sequence of pin movement and relative rotation of the two cylindrical parts. That is, a first portion of the tool is moved toward a second portion of the tool such that respective edges of the two portions are moved closer together, with the two portions having sleeve walls that serve a joining function to guide the two portions as they are moved closer together. The anal sphincter, for which the tool is configured, typically has an axial length of 2.0 cm to 2.5 cm. The tissue of the body opening typically has a thickness of 3 mm to 4 mm, and the spacing of the pins for the anal sphincter will typically be approximately 5 mm apart. The length of the pins will be such that the pins can pierce the internal tissue wall and engage the sphincter muscle, as described. FIG. 3 shows the corresponding movements of the tool portions with respect to the sphincter muscle tissue. The open spaces for putting the suture or staples are identified in the left side of FIGS. 2D, 2E, 2F.

A Modification of the First Implementation—Anal Canal

Figure 4:
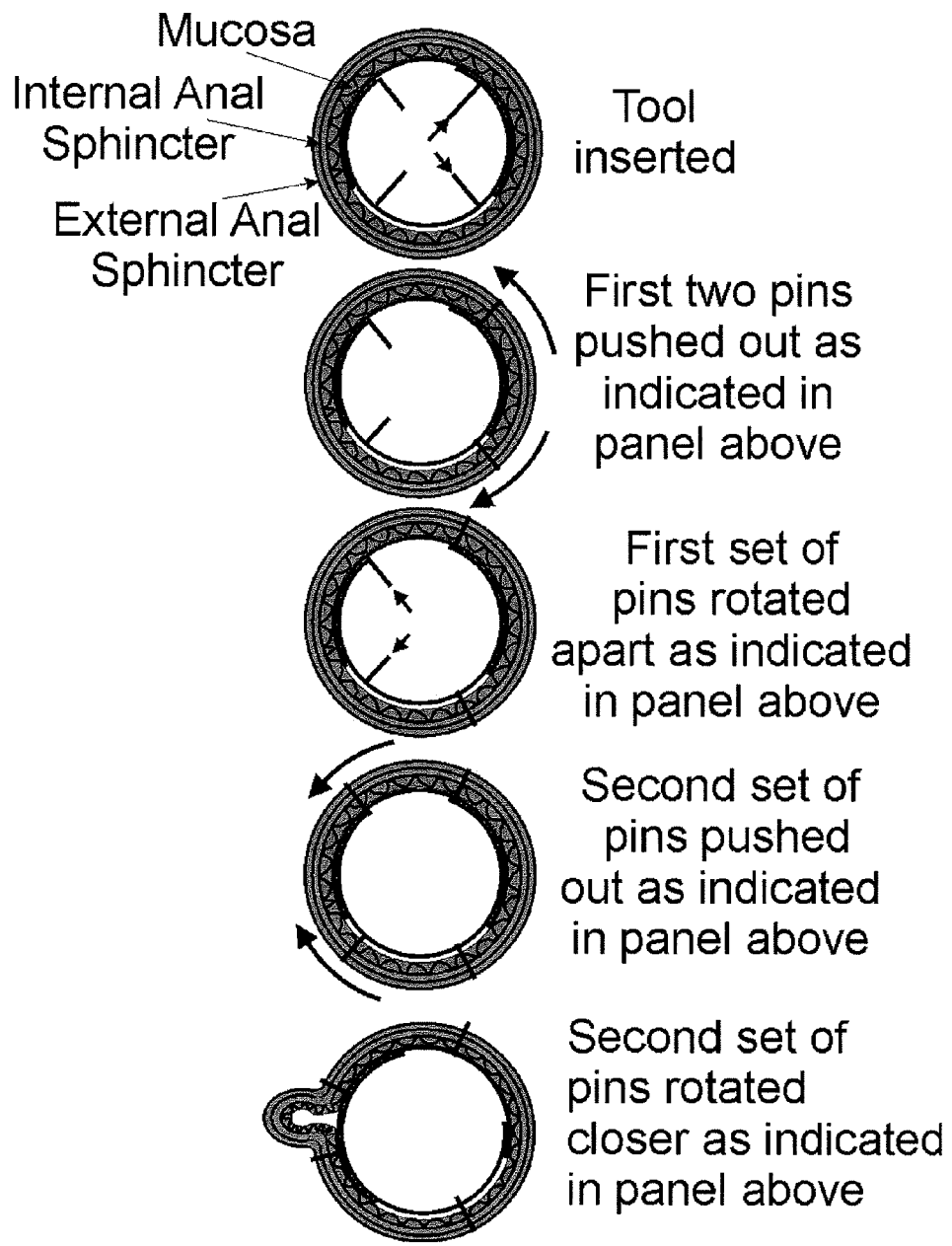
FIG. 4 is a cross-sectional depiction of a sphincter muscle that is plicated using a four-pin configuration of the tool illustrated in FIG. 1 and FIG. 2.

FIG. 4 shows how the same effect on the sphincter muscle in FIG. 3 may be achieved by use of a plication tool configured with four sets of pins. The FIG. 4 configuration includes four sets of pins positioned equi-spaced on either side of the plication open segments. In this implementation, the technique begins with the first two sets of pins that are most distant from the placation segment, which are pushed radially out to engage the sphincter muscle wall, and then the tool parts are rotated to move the first two pins away from each other and stretch the muscle between the first two sets of pins. Next, the remaining two sets of pins are pushed out to engage the sphincter muscle and the tool parts are circumferentially rotated to move the remaining pins closer together, with the first set of pins in the pushed out position. This will result in the same effect of bunching together part of the sphincter muscle to form a loop or pleat and to be plicated on one side while stretching the remaining muscle on the other side.

Third Implementation—Anal Canal

Figure 5:
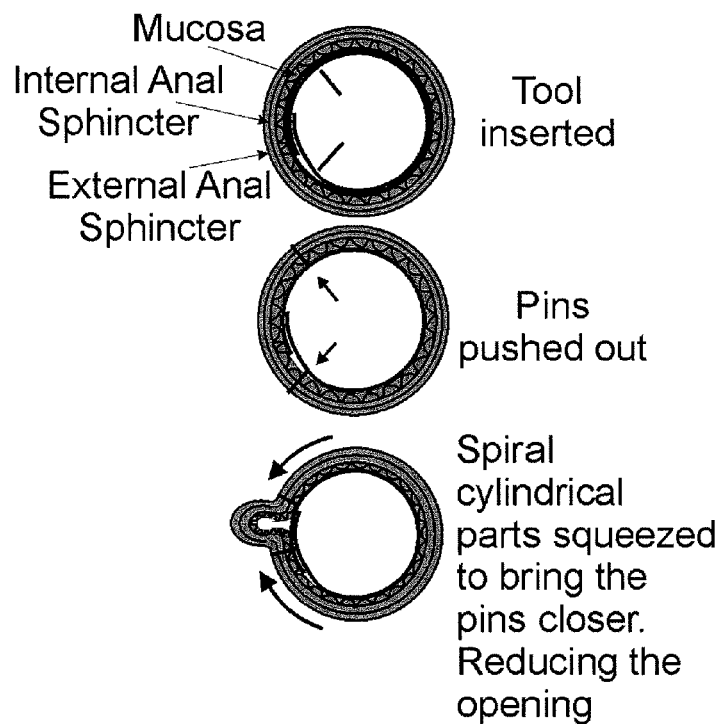
FIG. 5 is a cross-sectional depiction of a sphincter muscle that is plicated using a coiled tool to perform the sphincter treatment technique described herein.

This tool configuration, illustrated in FIG. 5, provides one single, unitary piece of material that is designed in such a fashion that the two "jaws" of the two concentric parts shown in FIG. 1 are on the same material. That is, the tool is in a coiled or helical arrangement to provide a spiral shape with the jaws partially overlapping. The openings between the two jaws are similar to the opening shown in FIG. 2. In the FIG. 5 configuration, instead of having two pieces that move concentrically to rotate and pull the two sets of pins together, the pins are brought together in a spiral, spring-like movement of the unitary material. Although the FIG. 5 configuration is described as "unitary", it should be understood that the tool may be comprised of more than one component or composition. Thus, different parts of the tool may be comprised of materials having different composition, such as plastic or metal or the like.

Fourth Implementation—Puborectalis Muscle

The anal canal muscle is a circular-shaped muscle with its plane perpendicular to the longitudinal axis of the canal. A plication tool for this muscle is configured so the pins move in the same plane. That is, the tools illustrated in FIGS. 1-5 provide concentric movement of the cylindrical parts that keeps the muscle parts in the proper position within the plane of the muscle as the parts are moved together. On the other hand, for U-shaped or semicircular-shaped muscles such as the puborectalis muscle, the plane which passes through the puborectalis muscle is at an angle to the longitudinal axis of the vagina. Therefore, in order to maintain the position of the ends of the muscle as they are brought closer together requires that the two articulating parts move in this plane. Therefore, the plication tool for the puborectalis muscle is configured in a skewed fashion as shown from a side view in the top two panels of FIG. 6. There is a slot at the appropriate angle on one part of the jaw and a guiding pin on the other part of the jaw that guides the two pieces to move in the proper direction. The FIG. 6 tool is designed to either be used for plication of either the left or right part of the puborectalis muscle. FIG. 6 shows a tool with pins on the right side of the tool. The width of the tool is designed to be wider than the space within the puborectalis muscle space so that the muscle can be engaged with the pins when they are pushed out.

Additional Depictions

Figures 7, 8:
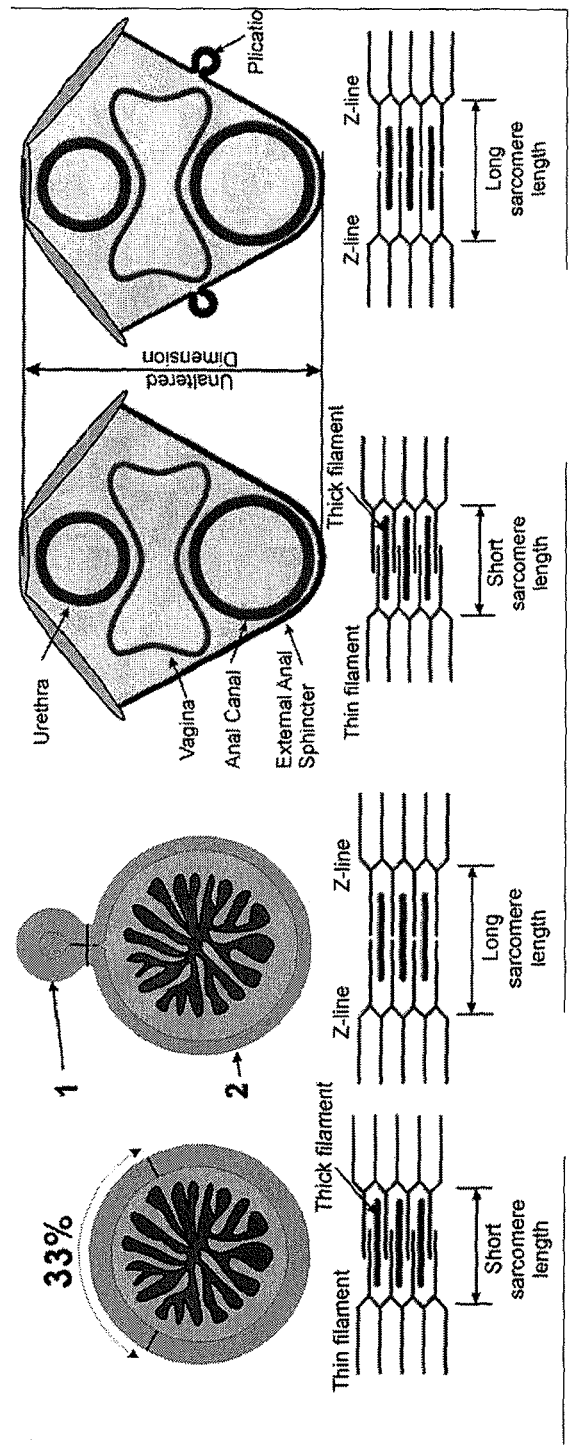
FIG. 7 is an illustration that shows the technique and tools described herein for treatment of fecal incontinence.
FIG. 8 is an illustration that shows the technique and tools described herein for treatment of vaginal laxity.

FIG. 7 is an illustration that shows the technique and tools described herein for treatment of fecal incontinence. A lateral band across the muscle loop in the right-hand illustration of FIG. 7 indicates a means for fixing the loop in place, such as a suture or surgical staple. FIG. 8 is an illustration that shows the technique and tools described herein for treatment of vaginal laxity. A lateral band across the muscle loop in the right-hand illustration of FIG. 8 indicates a means for fixing the loop in place, such as a suture or surgical staple.

Specific details are given in the description herein to provide a thorough understanding of the illustrated embodiments. It will be understood by those of ordinary skill in the art that the embodiments may be practiced without these specific details. For example, exemplary structures and constructions have been shown without unnecessary detail in order to avoid obscuring the embodiments. Thus, the surgical staples or sutures for fixing the loop of sphincter muscle are not shown in all the drawings, but will be readily known to those skilled in the art. In fact, different surgeons may prefer different means for fixing the sphincter muscle loop. In addition, dimensions and materials are specified for exemplary purposes only. Further, the headings provided herein are intended merely to aid in the clarity of the descriptions of various embodiments, and should not be construed as limiting the scope of the invention or the functionality of any part of the illustrated embodiments. For example, certain methods or components may be implemented as part of other methods or components, even though they are described under different headings.

The present invention has been described above in terms of presently preferred embodiments so that an understanding of the present invention can be conveyed. There are, however, many configurations for plication tools and treatment techniques not specifically described herein but with which the present invention is applicable. The present invention should therefore not be seen as limited to the particular embodiments described herein, but rather, it should be understood that the present invention has wide applicability with respect to treatment of dysfunctional sphincter muscles generally.

I claim:

1. A tool for use with a sphincter muscle associated with a bodily passage or opening, the tool comprising:
    a first portion through which at least one first pin is configured to be extended and retracted;
    a second portion through which at least one second pin is configured to be extended and retracted;
    a joining portion that guides movement of the first portion and the second portion such that in an insertion position the first portion and second portion are configured to be inserted into the bodily passage or opening and then in a plication position the first portion and second portion are configured to be moved in place relative to each other such that the first pin and the second pin can be moved closer together while providing a hollow space within the tool in the bodily passage or opening, and wherein in the insertion position, the first pin and the second pin are configured to be extended outwardly from the tool so as to engage the sphincter muscle, such that the first pin and second pin do not move relative to the sphincter muscle, and in the plication position, the first portion and second portion are configured to be moved relative to each other with the first and second pins extended, and thereafter, the first and second pins are configured to be retracted and the first and second portions can be moved relative to the sphincter muscle to permit removal of the tool from the bodily passage or opening.

2. The tool as in claim 1, wherein the first portion and second portion comprise separate cylindrical portions.

3. The tool as in claim 1, wherein the first portion, second portion, and joining portion are portions of a single unitary material.

* * * * *